United States Patent
Hotchkiss et al.

(10) Patent No.: US 9,314,494 B2
(45) Date of Patent: Apr. 19, 2016

(54) CRANBERRY XYLOGLUCAN OLIGOSACCHARIDE COMPOSITION

(75) Inventors: Arland T. Hotchkiss, Ambler, PA (US); Alberto Nunez, Dresher, PA (US); Christina Khoo, Duxbury, MA (US); Gary D. Strahan, Baltimore, MD (US)

(73) Assignees: The United States of America, as Represented by the Secretary of Agriculture, Washington, DC (US); Ocean Spray Cranberries, Inc, Lakeville-Middleboro, MA (US)

( * ) Notice: Subject to any disclaimer, the term of this patent is extended or adjusted under 35 U.S.C. 154(b) by 68 days.

(21) Appl. No.: 13/480,903

(22) Filed: May 25, 2012

(65) Prior Publication Data

US 2013/0316025 A1   Nov. 28, 2013

(51) Int. Cl.
```
A61K 36/45      (2006.01)
A61K 9/20       (2006.01)
A61K 31/70      (2006.01)
A61K 31/716     (2006.01)
A23L 1/30       (2006.01)
```

(52) U.S. Cl.
CPC .............. *A61K 36/45* (2013.01); *A23L 1/3002* (2013.01); *A61K 31/716* (2013.01); *A61K 2236/39* (2013.01)

(58) Field of Classification Search
CPC . A61K 36/45; A61K 31/716; A61K 2236/39; A01N 37/30; A01N 43/653; A01N 2300/00; A01N 43/40; A01N 3/16
See application file for complete search history.

(56) References Cited

U.S. PATENT DOCUMENTS

| | | | |
|---|---|---|---|
| 6,210,681 B1 * | 4/2001 | Walker et al. | 424/732 |
| 6,303,125 B1 | 10/2001 | Ofek et al. | |
| 6,843,993 B2 | 1/2005 | Ofek et al. | |
| 7,270,837 B2 * | 9/2007 | Vorsa et al. | 424/732 |
| 7,306,815 B2 * | 12/2007 | Gourdin et al. | 424/725 |
| 2002/0028260 A1 * | 3/2002 | Walker et al. | 424/766 |
| 2003/0149252 A1 * | 8/2003 | Gourdin et al. | 536/8 |
| 2004/0038367 A1 | 2/2004 | Yaoi et al. | |
| 2005/0175762 A1 * | 8/2005 | Richards et al. | 426/601 |
| 2006/0088610 A1 * | 4/2006 | Vorsa et al. | 424/732 |
| 2006/0280816 A1 * | 12/2006 | Gourdin et al. | 424/732 |
| 2007/0054877 A1 | 3/2007 | Stahl et al. | |
| 2007/0232565 A1 | 10/2007 | Sugahara | |
| 2007/0292539 A1 * | 12/2007 | Vorsa et al. | 424/732 |
| 2009/0226548 A1 | 9/2009 | Minatelli et al. | |
| 2010/0028469 A1 | 2/2010 | Alberte et al. | |
| 2010/0330054 A1 | 12/2010 | Priest et al. | |

(Continued)

FOREIGN PATENT DOCUMENTS

WO   2010078660 A1   7/2010

OTHER PUBLICATIONS

Seeram et al.: Total Cranberry Extract versus Its Phytochemical Constituents: Antiproliferative and Synergistic Effects against Human Tumor Cell Lines; Journal of Agricultural and Food Chemistry (2004), 52(9), 2512-2517.*

(Continued)

*Primary Examiner* — Patricia A Leith
(74) *Attorney, Agent, or Firm* — John D. Fado; Mark D. McNemar

(57) ABSTRACT

A composition prepared from a cranberry hull enzyme-treated composition which reduces or inhibits the adhesion of microorganisms to cells having α-Gal-(1-4)-Gal terminal oligosaccharide receptors for adhesion.

5 Claims, 7 Drawing Sheets

Anti-adhesion activity of cranberry material

(56) References Cited

U.S. PATENT DOCUMENTS

| | | |
|---|---|---|
| 2011/0021417 A1 | 1/2011 | Rhoades et al. |
| 2011/0059193 A1 | 3/2011 | Tournay et al. |
| 2011/0256279 A1 | 10/2011 | Roy et al. |

OTHER PUBLICATIONS

Vvedenskaya et al.: Characterization of Flavonols in Cranberry (Vaccinium macrocarpon) Powder;Journal of Agricultural and Food Chemistry (2004), 52(2), 188-195.*

Foo, L.Y. et al. "The Structure of cranberry proanthocyanidins which inhibit adherence of uropathogenic P-fimbriated *Escherichia coli* in vitro" (2000) Phytochemistry 54:173-181.

Howell, Amy B. et al. "A-type cranberry proanthocyanidins and uropathogenic bacterial anti-adhesion activity" (2005) Phytochemistry 66:2281-2291.

Hotchkiss Jr., A.T. et al. "Carbohydrate Characterization and Potential Bioactivity of Cranberry Xyloglucan Oligosaccharides" (2009) Power Point Presentation 1-24.

Hoffman, M. et al. "Structural Analysis of Xyloglucans in the primary cell walls of plants in the subclass Asteridae" (2005) Carbohydrate Research 340:1826-1840.

Ray, B. et al. "Structural Investigation of Hemicellulosic Polysaccharides from Argania Spinosa: Characterisation of a Novel Xyloglucan Motif" (2004) Carbohydrate Research 339:201-208.

Sims, I.M. et al., "Structural Characterisation of Xyloglucan Secreted by Suspension-Cultured Cells of Nicotiana" (1996) Carbohydrate Research 293:147-172.

Coleman, C. M. et al., Isolation and Identification of Antiadhesive Urinary Metabolites Produced as a Result of Cranberry Juice Consumption (2008) Phytochemistry Society of North America Annual Meeting.

* cited by examiner

CRANBERRY XYLOGLUCAN OLIGOSACCHARIDE COMPOSITION

BACKGROUND OF THE INVENTION

1. Field of the Invention

The present invention relates to a novel xyloglucan oligosaccharide composition designated anti-microbial adhesion inhibitory fraction A6, a composition containing said oligosaccharide composition containing anti-microbial adhesion inhibitory fraction A6, and methods of using said composition to at least reduce the adhesion of pathogens to animal cells, especially human and mammalian cells.

2. Description of the Related Art

Xyloglucan is well known as a major cross-linking polysaccharide in type 1 plant cell walls found in dicotyledonous and non-commelinoid monocotyledonous plants (Carpita and Gibeaut, Plant Journal, Volume 3, 1-30, 1993). With a $\beta$-(1-4)-glucan backbone, xyloglucan hydrogen bonds to the surface of cellulose microfibrils and forms a network that connects adjacent microfibrils in cell walls. The xyloglucan network is intermeshed with the pectin network of cell wall matrix polysaccharides (Carpita and Gibeaut, 1993 supra). This makes xyloglucan an important polysaccharide in the growth and development of primary cell walls (Carpita and McCann, "Biochemistry and Molecular Biology of Plants, Buchanan B. B., Gruissem, W., Jones, R. L., Eds.; American Society of Plant Physiologists, Rockville, Md., 52-108, 2000). There is a block-like structure in xyloglucan where a 6-11 sugar sequence is repeated throughout the polysaccharide. Therefore, carbohydrate structures are specific for plant taxonomic groups (Sims et al., Carbohydrate Research, Volume 293, 147-172, 1996; Vierhuis et al., Carbohydrate Research, Volume 332, 285-297, 2001; Ray et al., Carbohydrate Research, Volume 339, 201-208, 2004; Hoffman et al., Carbohydrate Research, Volume 340, 1826-1840, 2005). Three types of xyloglucan structures have been described with fucogalacto-xyloglucan the most commonly distributed in about half of the monocot taxonomic orders and all dicot orders except for the Solanales, Laminales, Gentianales and Ericales (Carpita and McCann 2000, supra; Hoffman et al., 2005, supra). Xyloglucan from these later orders contains arabino-xyloglucan structure. Small amounts of a third xyloglucan structure are also present in commelinoid monocots (grasses, bromeliads, palms, and cypresses) as randomly distributed single xylose substituents on a cellulosic backbone (Carpita and McCann, 2000, supra). A single letter nomenclature was developed to describe the sequence of xyloglucan substituents (Fry et al., Physiol. Plant., Volume 89, 1-3, 1993).

Cranberry juice is acidic (pH approximately 2.6 or lower) and rich in anthocyanins and tannins giving it an astringent taste (Holmes and Starr, Fruit Juice Processing Technology, Nagy, S., Chen, C. S., Shaw, P. E. (Eds.), AGSCIENCE, Auburndale, Fla., 515-531, 1993). The juice is prepared by milling and pressing after a hot (approximately 50 degree C. for about 1 hour) commercial pectinase maceration of the berries. Cranberry pectin has very high methoxy content, which requires a second hot commercial pectinase treatment following pressing and prior to juice filtration and concentration. Cranberry juice is considered a healthy juice. The proanthocyanidins have antioxidant properties (Uri-Sarda et al., Anal. Bioanal. Chem., Volume 394, 1545-1556, 2009) and were reported to inhibit adhesion of p-fimbriated *Escherichia coli* to uroepithelial cells (Howell et al., Phytochem., Volume 66, 2281-2291, 2005). P-fimbriated *E. coli* is the major cause of urinary tract infections which result in 8.3 million doctor office visits per year (Zopf and Roth, Lancet, Volume 347, 1017-1021, 1996). Cranberry juice was also reported to have prebiotic properties (Clifford et al., U.S. Patent Application No. 20090022849, 2009).

Recently, Coleman et al. (Presentation on Jul. 13, 2010 to the American Society of Pharmaconosy, St. Petersburg Beach, Fla.) fed pigs cranberry juice powder and isolated oligosaccharides or aminosugars from the urine that inhibited red blood cell agglutination using uropathogenic *E. coli*. The same $\alpha$-Gal-(1-4)-$\beta$-Gal receptor is required for red blood cell agglutination and p-fimbriated *E. coli* adhesion to uroepithelial cells (Howell et al. 2005, supra). Therefore, a carbohydrate, not derived from proanthocyanidins, was reported to have bacterial anti-adhesive properties (Coleman et al. 2010, supra). Pectic oligosaccharides inhibited the adhesion of verotoxigenic and enteropathogenic strains of *E. coli* to HT29 cells (Rhoades et al. J. Food Protect., Volume 71, 2272-2277, 2008). So there is precedence for plant cell wall oligosaccharides to have bacterial anti-adhesive properties. However, the structure for cranberry plant cell wall oligosaccharides is unknown and Coleman et al. (2010, supra) did not report how an oligosaccharide was absorbed in the gastrointestinal tract prior to urinary excretion.

Current therapeutic regimes for the neutralization and/or removal of bacteria and bacterial components from host organisms, such as humans and domestic livestock, are based largely on the use of antibiotics. Since their introduction in the 1940's, antibiotic drugs have proven effective for the treatment of many bacteria-related illnesses. However, their frequent misuse has given rise to antibiotic-resistant bacterial strains that have necessitated the development and implementation of increasingly more powerful drugs. Bacterial infections are increasing within hospitals, resulting in a dramatic increase in cases of patients with serious, and in some instances, life-threatening symptoms. By way of example, urinary tract infections (UTIs) have been a pervasive health care problem. UTIs are generally defined as the presence of >100,000 cells/mL of bacteria in the urine. UTIs are commonly caused by Gram-negative bacteria, particularly *Escherichia coli* (*E. coli*), and infect primarily women. This infection is enabled by the adherence and colonization of bacteria to urinary tract epithelial cells. Adherence by *E. coli* is performed by proteinaceous fibers (fimbriae) on the bacteria cell wall, which attach to specific oligosaccharide receptors on uroepithelial cells. Antibiotics are commonly prescribed for treatment, but often promote bacterial resistance. One in four women also encounter recurrence of the infection and are often found to be prone to such infections. Natural substances which could treat and prevent UTIs could be useful for those suffering this condition since antibiotic treatment, in many cases causes, as secondary vaginal yeast infection requiring a subsequent antifungal treatment.

There is a large literature on the role of cranberry phytonutrients in preventing or mitigating urinary tract infections (UTIs), and particularly the Gram negative uropathogenic bacterium *E. coli*, the most common cause of UTIs (Lavigne et al., Clinical Microbiology and Infection, Volume 14, 350-355, 2008; Ofeck et al., Advances in Experimental Medicine and Biology, Volume 408, 179-183, 1996; Ofeck et al, New England Journal of Medicine, Volume 324, 1599, 1991). Consumption of cranberries has been found to be somewhat effective in addressing UTI infections. Cranberry products can prevent adhesion of certain bacteria fimbriae to uroepithelial cells in the urinary tract, thereby reducing the ability of the bacteria to create an infection (DiMartino et al., World Journal of Urology, 2006); (Liu et al., Biotechnology Bioengineering, 2006). Proanthocyanidins, which are condensed tannins, found in the cranberry juice have been shown to inhibit *E. coli* adherence (Howell et al., Journal of Medicine, 1998). United States Patent Application 2009/0226548, published in 2009, states that some *E. coli* fimbriae bind specifically to D-mannose, unlike sucrose or fructose, which is metabolized very slowly in humans, therefore once consumed, D-mannose will enter the blood stream and quickly moves to excretion via the kidneys followed by entry into the bladder in urine. D-mannose once in urine will cause the bacterial fimbriae sensitive to D-mannose binding to attach to the D-mannose, rather than epithelial cells. This allows the body to flush the D-mannose bound *E. coli* bacteria from the body. In addition, D-mannose can reverse epithelial bound *E. coli* competitively interrupting the initial phases of urinary tract infection. To mitigate existing UTIs and prevent recurrence, regular consumption of cranberry in combinations with D-mannose will prevent bacteria from adherence, colonization and ultimately prevent an uncontrollable urinary tract infection. This reference further states that for this strategy to work, consumer compliance is necessary, Another treatment for bacterial and fungal infections is the use of cinnamon (*Cinnamonmum cassia*) extracts. The antimicrobial action of cinnamon can be partly attributed to the presence of cinnamaldehyde, eugenol, borneol, linool, and thymol, mainly antibacterial, and o-methylcinnamaldehyde, mainly antifungal.

There remains a need for nutrition and therapeutic compositions and methods for at least reducing inhibition of bacterial adhesion to human and mammalian cells and for reducing or inhibiting the invasion and infection of human and mammalian cells by pathogenic bacteria. The present invention described below includes such compositions and methods which are different from related art compositions and methods.

SUMMARY OF THE INVENTION

It is therefore an object of the present invention to provide a composition prepared from enzyme treated cranberry hulls from *Viccinium macrocarpon* which at least reduces the adhesion of microorganisms to cells having α-Gal-(1-4)-Gal terminal oligosaccharide receptors for adhesion.

Another object of the present invention is to provide a composition prepared from enzyme treated cranberry hull from *Viccinium macrocarpon* wherein in said composition comprises an acetylated, neutral-sugar-rich polysaccharide having a weight—average molar mass of approximately $10.2 \times 10^3 \pm 2$ Da, a Z-average hydrodynamic radius of approximately $2.0 \pm 0.2$ nm, and a weight—average intrinsic viscosity of approximately $0.048 \pm 0.001$ dL/g.

A still further object of the present invention is to provide a method for preventing adhesion of bacteria to cells having α-Gal-(1-4)-Gal terminal oligosaccharide receptors for adhesion wherein a composition having an acetylated, neutral-sugar-rich polysaccharide having a weight—average molar mass of approximately $10.2 \times 10^3 \pm 2$ Da, a Z-average hydrodynamic radius of approximately $2.0 \pm 0.2$ nm, and a weight—average intrinsic viscosity of approximately $0.048 \pm 0.001$ dL/g is administered to cells having α-Gal-(1-4)-Gal terminal oligosaccharide receptors for adhesion.

Further objects and advantages of the present invention will become apparent from the following description.

Sugar rings are numbered from the non-reducing end (left to right) for A, B, and C ions and from the reducing end for the X, Y, and Z ions (right to left). Greek letters are used to distinguish fragments from branches to the central backbone chain, with alpha (top left) and beta (bottom center) used in this structure. Superscript numbers are given for cross-ring cleavage positions within the sugar rings.

Figure 5A:
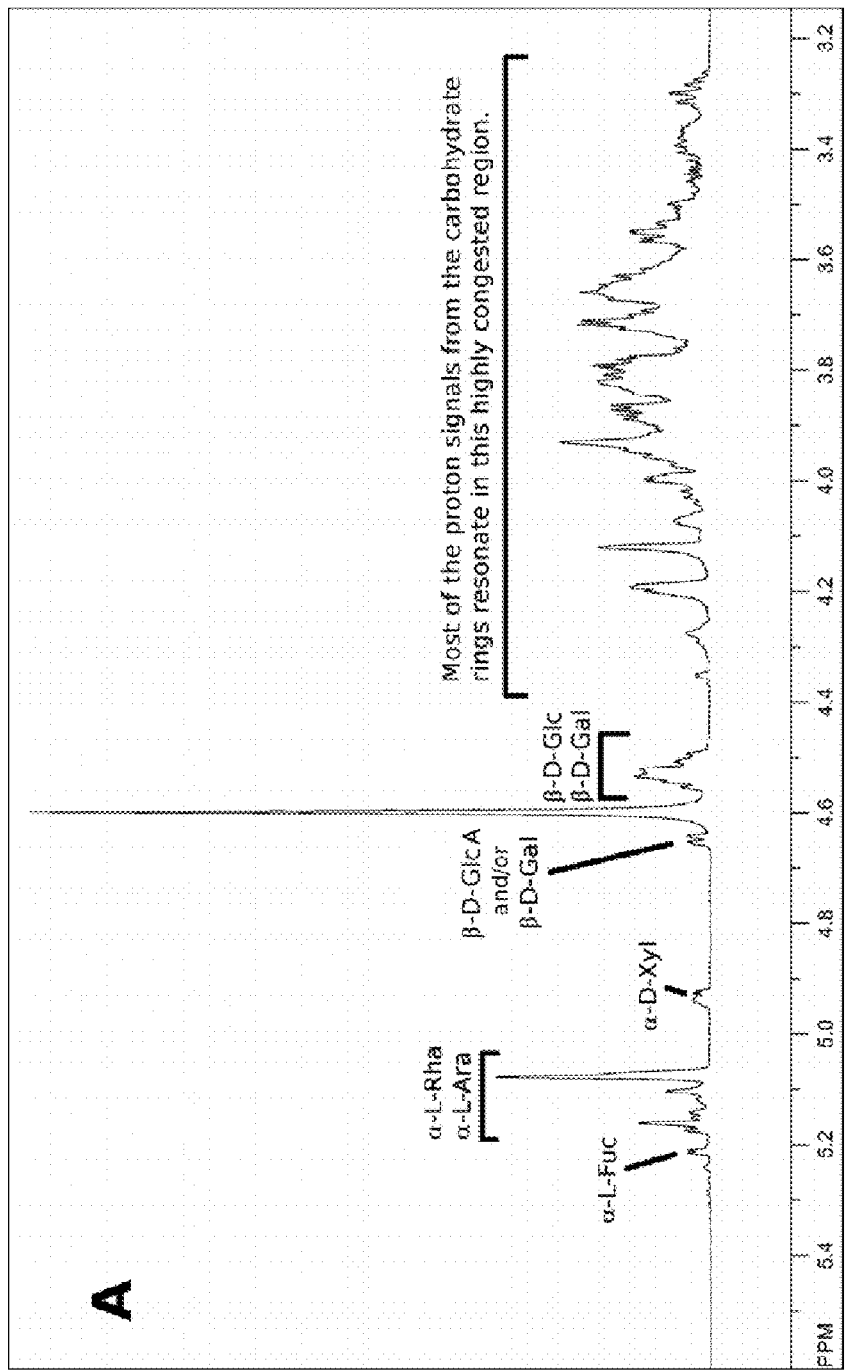
Figures 5B, 5C:
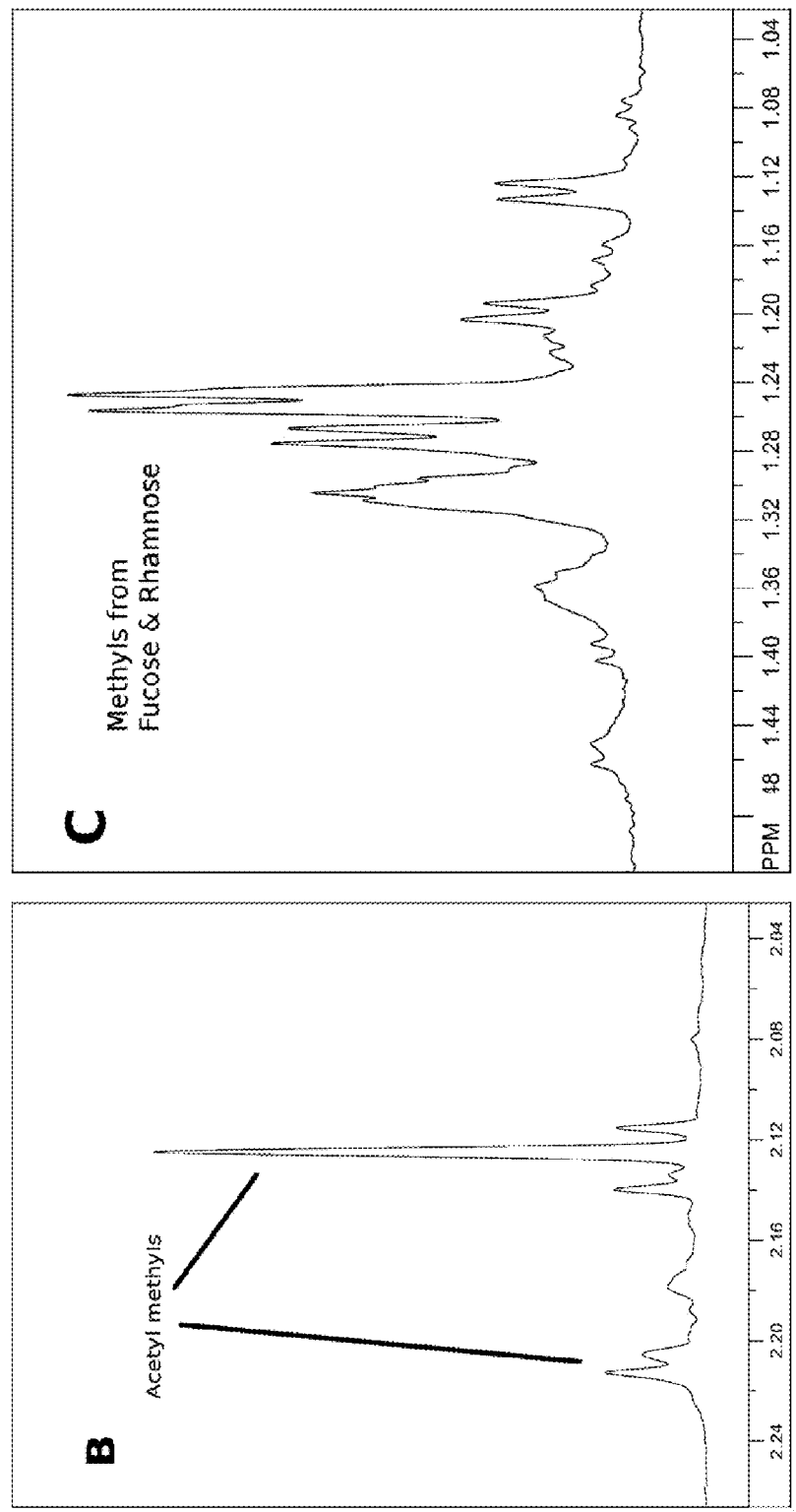

FIGS. 5A-C are NMR spectrum of fraction A6.

Figure 6:
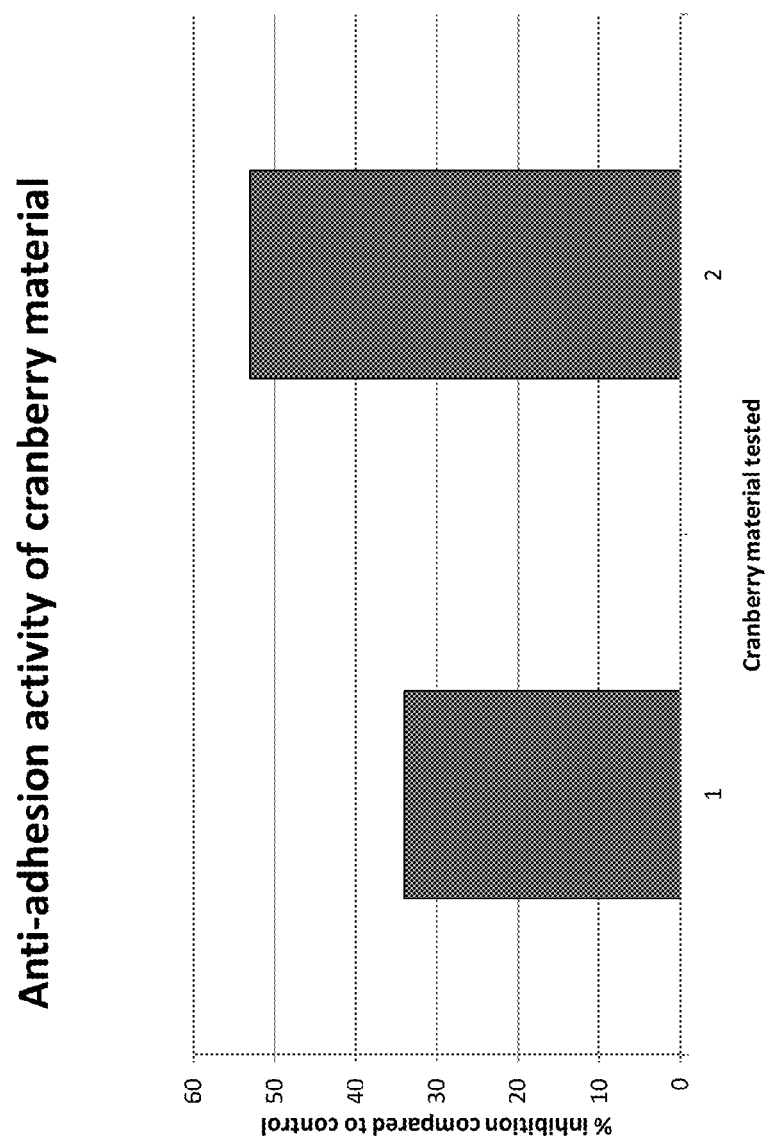

FIG. 6 is a graph showing anti-adhesion activity of cranberry fractions from *Vaccinium macrocarpon*. The A1 fraction is bar 1 (left bar) and the anti-microbial adhesion inhibitory fraction A6 is bar 2 (right bar).

DETAILED DESCRIPTION OF THE INVENTION

The present invention provides a composition prepared from a cranberry hull enzyme-treated composition using the cranberry *Viccinium macrocarpon*. The composition of the present invention comprises a suitable carrier and an effective amount of the isolated anti-microbial adhesion inhibitory fraction as the active ingredient for use an agent to reduce or inhibit the adhesion of microorganisms to cells having α-Gal-(1-4)-Gal terminal oligosaccharide receptors for adhesion.

The isolated adhesion inhibitory fraction is designated as A6 and is characterized by: A6 contains an acetylated, neutral-sugar-rich polysaccharide having a weight—average molar mass of approximately $10.2 \times 10^3 \pm 2$ Da, a Z-average hydrodynamic radius of approximately $2.0 \pm 0.2$ nm, and a weight—average intrinsic viscosity of approximately $0.048 \pm 0.001$ dL/g. The monosacchride composition of A6 was dominated by glucose, arabinose, and xylose with very little galacturonic acid and rhamnose present, which indicates that the polysaccharide fragment is a hemicellulose and possibly a xyloglucan.

The composition of the present invention can be administered to a patient orally. Generally the concentration of the isolated anti-microbial adhesion inhibitory fraction is that amount which reduces the adhesion of bacterial cells to mammalian cells, especially human cells, determination of which is well within the ordinary skill in the art.

For purposes of the invention, the following are definitions of certain terms to be used hereinafter.

As used in the specification and claims, the singular form "a", "an", and "the" include plural references unless the context clearly dictates otherwise. For example, the term "a cell" includes a plurality of cells, including mixtures thereof.

As used herein, cranberry is understood to be *Viccinium macrocarpon*.

The term xyloglucan is used to describe a group of polysaccharides referred to as hemicelluloses. Xyloglucans contain a backbone of 1,4-linked β-D-glucopyranosyl residues in which O4 is in the equatorial orientation.

The term isolated, purified, or biologically pure as used herein, refer to material that is substantially or essentially free from components that normally accompany it as found in its native state. In an exemplary embodiment, purity and homogeneity are determined using analytical chemistry techniques such as polyacrylamide gel, electrophoresis, or high performance liquid chromatography.

As used herein, the term pathogen refers to non-beneficial bacteria, virus, fungi, monocellular or multicellular parasites, for example *E. coli*, e.g. verocytotoxic *E. coli* (VTEC), enteropathogenic *E. coli* (EPEC), enterotoxigenic *E. coli* (ETEC), or enteroaggregative *E. coli* (EAggEC), *Staphylococcus aureus*, methicilin-resistant *Staphylococcus aureus* (MRSA), *Clostridium difficle*, Sulphate Reducing bacteria, e.g. *Desulfovibrio* sp., eg. *Desulfovibrio desulfuricans* or *Desulfovibrio piger*.

As used herein, the term "control", or "controlling" as in e.g., the phrase: the control of *E. coli*, controlling *E. coli*, controlling *E. coli* populations, or controlling *E. coli* infection" or any grammatically equivalent expression, refers to any means for preventing infection or infestation, reducing or diminishing the population of already infected areas or organisms, or elimination of the population of *E. coli* or other species whose control is desired. Controlling as used herein refers to any indication of success in prevention, elimination, reduction, or amelioration of *E. coli*, an *E. coli* infection, or a population of *E. coli*.

A medicament, nutritional or pharmaceutical composition of the invention is defined as a composition having at least one active ingredient of the present invention and a suitable carrier. A suitable carrier is defined as any substance that does not cause significant irritation to a living cell or organism and does not abrogate the biological activity and properties of the administered active ingredient of the present invention.

A therapeutically effective amount is as used herein refers to the amount necessary to elicit the desired biological response. As will be appreciated by those of ordinary skill in this art, the effective amount of a bioactive agent may vary depending on such factors as the desired biological endpoint, the bioactive agent to be delivered, the composition of the encapsulating matrix, the target tissue, etc.

The term "fraction" means as used herein refers to any HPLC eluted fraction from a cranberry hull enzyme-treated concentrate that is capable of controlling *E. coli* populations in a living organism or a population of living cells.

The term "urinary tract infection or "UTI" is refers to a bacterial infection that affects any part of the urinary tract. When bacteria get into the bladder or kidney and multiply in the urine, they cause UTI. The most common type of UTI is a bladder infection which is also called cystitis.

The term adhesion refers to the general aggregation of bacteria to each other, to other cell surfaces, and to non-cell surfaces through adhesion molecules on the surface of the bacteria.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

P-fimbrial adhesion molecules bind specifically to a group of receptors identified as P-blood group antigens. The receptors are present on the surface of various types of human cells such as urinary tract epithelium and red blood cells, that mediate the attachment of bacteria and subsequent colonization of the epithelium of the urinary tract. P-fimbriated *E. coli* cause agglutination (HA) of human red blood cells (RBC) (Ofeck and Doyle, Bacterial Adhesion to Cells and Tissues, Chapman and Hall, Ltd., London, 357-365, 1994).

The present invention provides a medicament, nutritional or pharmaceutical composition and method for at least reducing the adhesion of bacteria by treating with a bacterial adhesion reducing amount of the isolated adhesion inhibitory fraction designated as A6 in a suitable carrier. This composition can be administered in various ways suitable for therapy. The active ingredient, A6 can be administered alone or as an active ingredient in combination with pharmaceutically acceptable carriers, diluents, adjuvants, and vehicles. The composition will generally be administered orally. Conventional methods such as administering the compounds as tablets, suspensions, solutions, emulsions, capsules, powders, syrups, and the like are usable. Known techniques to deliver the anti-adhesion composition orally or intravenously and retain biological activity are preferred. Formulations that can be administered subcutaneously, topically, or parenterally or intrathecal and infusion techniques are also contemplated by the present invention as well as suppositories and implants.

The pharmaceutically acceptable carriers, diluents, adjuvants and vehicles as well as implant carriers generally refer to inert, non-toxic solid or liquid fillers, diluents, or encapsulating material not reacting with the active ingredients of the invention. The pharmaceutical formulations suitable for injection include sterile aqueous solutions or dispersions and sterile powders for reconstituition into sterile injectable solutions or dispersions. The carrier can be a solvent or dispersing medium containing for example, water, ethanol, polyol such as glycerol propylene glycol, liquid polyethylene glycol, etc., and suitable mixtures thereof and vegetable oils.

Proper fluidity can be maintained by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters, such as isopropyl myristate, may also be used as solvents for compound compositions. Additionally various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, etc. It may be desirable to include isotonic agents, for example sugars, sodium chloride, etc. Prolonged absorption of the injectable pharmaceutical form can be brought about by the use of agents delaying absorption, for example, aluminum monosterate, gelatin, etc. Any vehicle, diluents or additive used would have to be compatible with the anti-microbial adhesion fraction A6 of the invention. The choice of delivery system is well within the ordinary skill in the art.

Identification of xyloglucans in the anti-microbial adhesion inhibitory fraction A6 of the present invention was carried out using carbohydrate analysis, high performance size exclusion chromatography, MALDI-TOF/TOF MS, and nuclear magnetic resonance spectroscopy. The active xyloglucan preparation of the present invention is designated anti-microbial adhesion fraction A6 which includes an arabinoxyloglucan with SSGG structure as the predominant block sequence. This is the first member of the Ericales with this type of xyloglucan structure, but only the second plant in the order to have the xyloglucan characterized. A new xyloglucan heptasaccharide was characterized as SSG and GSS oligosaccharide structure. The SSG/GSS xyloglucan heptasaccharide and SSGG xyloglucan octasaccharides were the most abundant ions in the cranberry MALDI-TOF MS spectra. NMR confirmed the cranberry xyloglucan structure elucidated with mass spectrometry. The cranberry xyloglucan oligosaccharides were active in blocking the adhesion of uropathogenic and verotoxigenic strains of E. coli to human epithelial cells.

A method for isolating the anti-microbial adhesion fraction A6 from cranberry includes the steps of treating cranberry hulls with Klerzyme 150 pectinase (DSM Food Specialities) or other equivalent pectinase in this family of enzymes. Treatment typically is in the range of 100-140° F. for fruit depectinization. The dose for a 30-45 minute depectinization is about 0.035 to 0.055 percent by weight (so 0.035-0.055 pounds enzyme per 100 pounds fruit) and this can be adjusted for changes is in time or amount of enzyme during cranberry depectinization. Debris and other particulate matter is removed by decantation, centrifugation or other similar methods. The liquid is then spray dried to produce the cranberry powder and to produce a fraction A1. Fractionation of A1 was accomplished by utilizing a Biotage FLASH-40 system, converted to accept Biotage SNAP KP-C18-HS 120 g cartridges, fitted with a SNAP KP-C18-HS 12 g samples. Approximately 20 grams of fraction A1 was dissolved in about 200 ml of deionized water (DI). About 50 ml (±5 g) of the solution was loaded to the pre-conditioned (eluted with about 300 ml methanol followed by about 300 ml DI water) C18-column. Fractionation was initiated by eluting column first with about 500 ml of DI water, following with about 500 ml of an about 15% methanol/water (V/V) mixture (flow rate: approximately 35 ml/min), to produce fraction A2. The remaining phenolic content was washed from the column with about 500 ml of methanol. The column was re-conditioned by washing it with about 500 ml of DI water before loading it again with more of the A1 solution (about 50 ml). This process was repeated a total of 4 times and the approximately 15% methanol/water parts were combined to produce fraction A2. Fraction A2 was dried; first by the removal of the methanol under vacuum (Buchi Laboratory Equipment), followed by the freeze drying of the aqueous solution to yield about 4.97 g of a pink colored powder. Analysis of A2 observed an unknown peak that eluted at approximately 6.7 min from a HPX-87C HPLC column, using refractive index detection. Fraction A2 was further purified by Sephadex LH 20 chromatography to eliminate the remainder of the phenolic pigments. Therefore, fraction A2 (approximately 4.8 g) was dissolved in approximately 60 ml of DI water and the mixture was loaded on a 45×300 mm Sephadex LH20 column (pre-condition by about 500 ml of DI water). The column was eluted with about 500 ml of DI water (using a Masterflex L/S pump—model 7014-52 at a flow rate of about 2.5 ml/min) to produce the purified fraction A6. The remaining phenolic content was washed from the column with an approximately 75% acetone/water solution (about 500 ml). Fraction A6 was freeze dried to produce approximately 4.32 g of an off-white (pinkish tint) crystalline powder.

Example 1

Xyloglucan-oligosaccharides with a degree of polymerization (DP) of approximately 7 to 9 were purchased from Megazyme (Bray, Ireland). A cranberry hull enzyme-treated concentrate fraction designated A1 was produced using Klerzyme 150 pectinase (DSM Food Specialties) during cranberry depectinization. Fractionation of A1 by C18 Flash Chromatography, produced about a 15% methanol fraction (A2). An unknown peak that eluted at approximately 6.7 min from a HPX-87C HPLC column using refractive index detection was observed in the A2 fraction. There was a pink color associated with A2 that was reduced with LH20 gel column chromatography to eliminate phenolic pigments, which produced A6 In detail, cranberry hulls were treated with Klerzyme 150 pectinase (DSM Food Specialities) or other equivalent pectinase in this family of enzymes. Treatment typically was in the range of approximately 100-140° F. for fruit depectinization. The dose for about a 30-45 minute depectinization was about 0.035 to 0.055 percent by weight (so approximately 0.035-0.055 pounds enzyme per approximately 100 pounds fruit) and this can be adjusted for changes in time or amount of enzyme by one knowledgeable about the method. Debris and other particulate matter were removed by decantation, centrifugation or other similar methods. The liquid was then spray dried to produce the cranberry powder fraction A1. Fractionation of A1 was accomplished by utilizing a Biotage FLASH-40 system, converted to accept Biotage SNAP KP-C18-HS 120 g cartridges, fitted with a SNAP KP-C18-HS 12 g samplets. A1 (approximately 20 grams) was dissolved in 200 ml of deionized water. Approximately 50 ml (±5 g) of the solution was loaded to the pre-conditioned (eluted with about 300 ml methanol followed by about 300 ml DI water) C18-column. Fractionation was initiated by eluting column first with about 500 ml of DI water, following with about 500 ml of an approximately 15% methanol/water mixture (flow rate: 35 ml/min), to produce fraction A2. The remaining phenolic content was washed from the column with about 500 ml of methanol. The column was re-conditioned by washing it with about 500 ml of DI water before loading it again with more of the A1 solution (approximately 50 ml). This process was repeated a total of 4 times and the approximately 15% methanol/water parts were combined to produce fraction A2. Fraction A2 was dried; first by the removal of the methanol under vacuum (Buchi Laboratory Equipment), followed by the freeze drying of the aqueous solution to yield approximately 4.97 g of a pink colored powder. Analysis of A2 observed an unknown peak that eluted at approximately 6.7 min from a HPX-87C HPLC column, using refractive index detection. Fraction A2 was further purified by Sephadex LH 20 chromatography to eliminate the remainder of the phenolic pigments. Therefore, fraction A2 (approximately 4.8 g) was dissolved in 60 ml of DI water and the mixture was loaded on a 45×300 mm Sephadex LH20 column (pre-condition by about 500 ml of DI water). The column was eluted with about 500 ml of DI water (using a Masterflex L/S pump—model 7014-52 at a flow rate of approximately 2.5 ml/min) to produce the purified fraction A6. The remaining phenolic content was washed from the column with an approximately 75% acetone/water solution (about 500 ml). Fraction A6 was freeze dried to produce approximately 4.32 g of an off-white (pinkish tint) crystalline powder.

Neutral sugar content (NS), galacturonic acid content (GA), degree of esterification (DE) and degree of acetylation (DA) were determined as reported previously (Fishman et al. 2008) except that the NS (Glucose standard) was used as the basis for the DA instead of the GA. Monosaccharide analysis by high-performance anion-exchange chromatography with pulsed amperometric detection (HPAEC-PAD) following methanolysis was according to the procedure reported previously (Zhao et al., Alternative Therapies, Volume 14, 34-38, 2008). Unhydrolysed oligosaccharides were also separated by HPAEC-PAD according to the procedure reported by Rhoades et al., 2008, supra.

High performance size exclusion chromatography was used to perform carbohydrate analysis of the A1 fraction produced by commercial pectinase treatment of cranberry hulls. Cranberry samples of approximately 10-20 mg/ml were dissolved in a mobile phase containing approximately 0.05 M $NaNO_3$ and approximately 0.01% $NaN_3$, stirred overnight in a cold room, centrifuged at approximately 50,000 g for about ten minutes and filtered through an approximately 0.22 or 0.45 micrometer Millex HV filter (Millipore Corp., Bedford, Mass.). The flow rate for the solvent delivery system, model 1100 series degasser, auto sampler and pump (Agilent Corp.), was set at approximately 0.7 mL/minute. The injection volume was approximately 200 μL. Samples were run in triplicate. The column set consisted of one PL Aquagel OH-40 and two OH-30 size exclusion columns (Polymer Laboratories, Amherst, Mass.) in series. The column temperature was controlled in a water bath set at approximately 35 degrees C. Column effluent was detected with a HELEOS II multi-angle laser light scattering photometer (MALLS) (Wyatt Technology, Santa Barbara, Calif.), in series with a model Viscostar II differential pressure viscometer (DPV) (Wyatt Technology, Santa Barbara, Calif.), and an Optilab rEX interferometer (RI) (Wyatt Technology). Electronic outputs from these three detectors were processed with ASTRA™ software (Wyatt Technology).

Carbohydrate analysis of the A1 fraction produced by commercial pectinase treatment of cranberry hulls contained high-methoxy pectin fragments and significant amounts of neutral sugar-rich material (Table 1). The A2 fraction was derived from A1 by methanol elution from a reversed-phase HPLC column. Apparently, the methanol was not completely removed from this fraction since A6 had significantly more methanol than was theoretically possible as pectic methyl-esters (Table 1). The most purified of the cranberry fractions (A6) consisted of an acetylated, neutral-sugar-rich polysaccharide with a weight-average molar mass of approximately 10,200 Da (Table 2). The z-average hydrodynamic radius and weight—average intrinsic viscosity were consistent with the low molecular weight of A6 (Table 2). The molecular weight values for A1 and A2 were also low compared to most polysaccharides, but A6 had the lowest molecular weight of the three cranberry fractions.

TABLE 1

Carbohydrate Analysis of Cranberry Fractions (Mole %).

| Sample | GA | MeOH | HAc | DE | DA | NS |
|---|---|---|---|---|---|---|
| A1 | 32.6 | 3.5 | 0.9 | 59.8 | 4.9 | 53.1 |
|  | (1.2) | (0.1) | (0.02) | (3.2) | (0.2) | (0.8) |
| A2 | 4.6 | 22.0 | 10.2 | 2632.6 | 36.5 | 83.7 |
|  | (1.0) | (1.3) | (0.5) | (793.23) | (2.0) | (0.6) |
| A6 | 3.2 | 23.6 | 13.6 | 4106.4 | 48.7 | 84.1 |
|  | (0.7) | (2.2) | (0.1) | (1318.6) | (0.3) | (0.2) |

GA = Galacturonic Acid,
MeOH = Methanol,
HAc = Acetate,
DE = Degree of Esterification
DA = Degree of Acetylation,
NS = Neutral Sugar

TABLE 2

Global Solution Properties of Cranberry Fractions

| Sample | Mwe–3 | Rhz (nm) | Ivw (dL/g) |
|---|---|---|---|
| A1 | 34.5 (9) | 3.3 (.2) | 0.61 (.005) |
| A2 | 30.0 (3) | 3.2 (.8) | .043 (.01) |
| A6 | 10.2 (2) | 2.0 (.2) | .048 (.001) |

Mwe–3 = Weight-Average Molar Mass × 10–3 Da
Rhz = Z-Average Hydrodynamic Radius
Ivw = Weight-Average Intrinsic Viscosity The monosaccharide composition of A2 and A6 cranberry fractions was dominated by glucose, arabinose and xylose with very little galacturonic acid and rhamnose present in these fractions (Table 3). This indicated that the polysaccharide fragment was a hemicellulose and possibly xyloglucan. The A1 fraction contained a significant amount of homogalacturonan, but the low levels of rhamnose detected indicated that the neutral sugars present were not pectic side-chains.

TABLE 3

Monosaccharide Composition of Cranberry Fractions (Mole %).

| Sample | Glc | Ara | Gal | Xyl | Rha | Fuc | GalA | GlcA |
|---|---|---|---|---|---|---|---|---|
| A1 | 25.36 | 10.69 | 7.38 | 6.6 | 0.34 | 0.16 | 49.43 | 0.05 |
| A2 | 45.97 | 28.49 | 4.56 | 16.95 | 0.48 | 0.35 | 3.16 | 0.04 |
| A6 | 50.33 | 25.72 | 4.41 | 14.79 | 0.54 | 0.37 | 3.66 | 0.18 |

Figure 1:
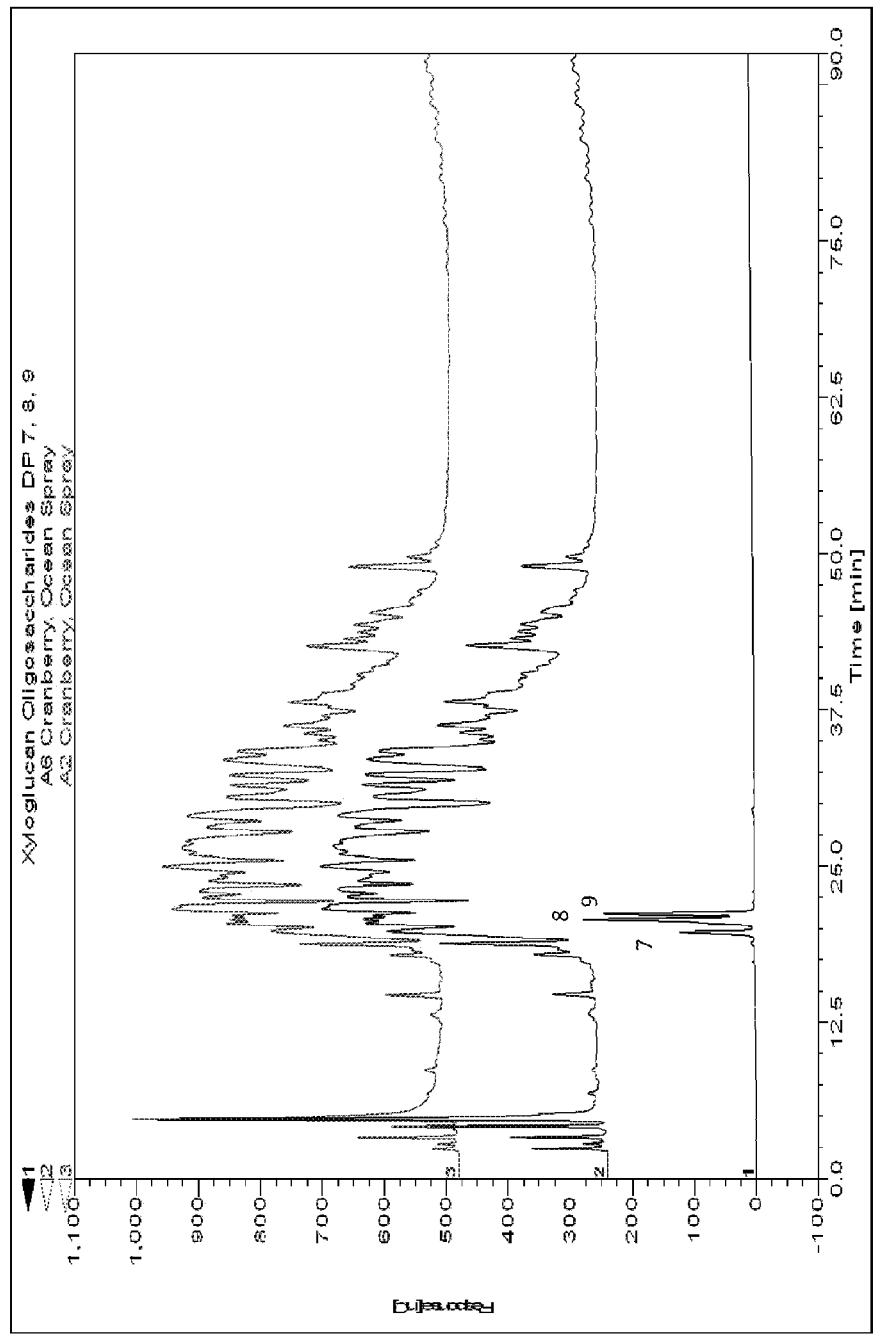
FIG. 1 is a graph showing oligosaccharide analysis of cranberry fractions. The DP of the xyloglucan oligosaccharides is indicated above each peak.

Glc = glucose,
Ara = arabinose,
Gal = galactose,
Xyl = xylose,
Rha = Rhamnose,
Fuc = fucose,
GalA = galacturonic acid,
GlcA = glucuronic acid A series of oligosaccharide peaks were present in A2 and A6 cranberry fraction HPAEC-PAD chromatograms (FIG. 1). Xyloglucan standard oligosaccharides were consistent with the retention times of some of these peaks. However, the structure of the Megazyme xyloglucan oligosaccharides was galacto-xyloglucan. For example, the DP 7 xyloglucan consisted of a cellotetraose backbone and three single xylose substituents attached to three of the glucose residues. The DP 8 and DP 9 xyloglucan standards had one or two of the xylose residues substituted with a galactose residue, respectively. This xyloglucan structure is typical of fucogalacto-xyloglucan without fucose. However, relatively low amounts of galactose were detected in the A2 and A6 monosaccharide composition. This indicated that the cranberry xyloglucan structure might differ from fucogalacto-xyloglucan since the majority of the A2 and A6 oligosaccharide peaks did not agree with the xyloglucan standard retention times.

Example 2

Matrix-assisted laser desorption ionization mass spectrometry with automated tandem time of flight mass spectrometry (MALDI-TOF/TOF MS) was used to determine xyloglucan structure. MALDI-TOF/TOF MS fragmentation of selected ions of oligosaccharides were acquired with a 4700 Proteomics Analyzer mass spectrometer (Applied Biosystems, Framingham, Mass.) in the positive reflectron mode. Spectra were obtained by averaging approximately 100 and approximately 2500 acquired spectra in the MS and MS/MS modes, respectively. Collision induced dissociation (CID) with air at an approximately $1 \times 10^{-6}$ Torr, at approximately 1

KeV acceleration voltage was used for obtaining the MS/MS spectra for selected oligosaccharides. Conversion of TOF to mass (Da) for the monoisotopic ions, [M+Na]$^+$, was based on calibration of the instrument with a peptide standard calibration kit (Applied Bio systems). Oligosaccharide samples (approximately 3-5 mg) were dissolved in about 1 mL of water and cleaned with CarboPrep 90 graphitized carbon cartridges, about 3 mL, approximately 250 mg (Restek, Bellefonte, Pa.). The cartridges were first conditioned by passing approximately 3 mL acetonitrile:water (approximately 50:50 V/V) and then washed about 4 times with approximately 3 mL water. After conditioning, the oligosaccharide solution was passed through the graphitized carbon cartridge, washed about 3 times with approximately 3 mL of water and the water wash was discarded. The oligosaccharides were eluted with about 1 ml of acetonitrile:water (approximately 30:70 V/V), approximately 0.1% trifluoro-acetic acid (TFA). From this solution, approximately 2 μL were mixed with approximately 10 μL of a solution of 2,5-dihydroxybenzoic acid (approximately 10 mg/mL in acetonitrile:water (approximately 50:50 V/V), approximately 0.1% TFA), and spotted onto a MALDI plate for analysis.

MALDI-TOF mass spectrometry of the A6 fraction produced a series of pseudomolecular ions (FIG. 2) that were consistent with xyloglucan structure (Table 4). The ions at approximately m/z 791 and 923 were previously reported in tobacco suspension culture xyloglucan with SGG and/or XXG, and SXG and/or XSG structure, respectively (Sims et al., 1996). The ions at approximately 1085, 1217, 1379, and 1525 were reported for Argan (Ericlaes) tree xyloglucan with Hex$_4$-Pent$_3$, Hex$_4$-Pent$_4$, Hex$_5$-Pent$_4$, and Hex$_5$-Pent$_4$dHex composition, respectively (Ray et al., 2004, supra). The 1525 ion had XUFG xyloglucan structure (Ray et al., 2004, supra). Otherwise the Argan tree xyloglucan was reported to consist of fucogalacto-xyloglucan structure. The 1217 ion was very abundant in the cranberry MALDI-TOF MS spectrum and has been reported to have XXSG structure previously for Oleander and olive fruit xyloglucan (Vierhuis et al., 2001, supra; Hoffman et al., 2005, supra). However, the diagnostic ions for XXSG structure (Vierhuis et al., 2001, supra) were not present in the cranberry MALDI-TOF/TOF spectrum for m/z approximately 1217.37 (FIG. 3B). Therefore, the SSGG xyloglucan structure appeared to be the predominant cranberry xyloglucan structure as was reported for m/z approximately 1217 in tobacco (Sims et al., 1996). The approximately 1127, 1259, 1289, 1331, and 1421 ions were previously reported as the acetylated xyloglucan oligosaccharide compositions in tobacco (Table 4). For the approximately 1289 and 1331 ions, XLXG and/or XXLG, and UXGGG and/or XUGGG structure, respectively, was assigned as reported previously (Sims et al., 1996). However, due to the relatively low amount of galactose in the cranberry xyloglucan, these ions could have XSGGG-Ac and XSGGG-Ac$_2$ structure. The Hex$_2$-Pent$_n$dHexHexAMe xyloglucan composition series has never been reported previously but is similar to the XUFG structure reported for the Argan tree (Ericales) xyloglucan and the xylan oligosaccharides containing 4-O-methyl-glucuronic acid from the same source (Ray et al. 2004, supra). One of the most abundant cranberry ions, approximately 1055, also has never been reported previously for xyloglucan structure and was used for further MS/MS structural analysis investigation. The two most abundant cranberry ions, approximately 1055 and 1217, were also detected as their potassiated forms ([M+K]$^+$) at m/z=approximately 1071 and 1233, respectively.

Oligosaccharide analysis by MALDI-TOF/TOF MS produced a set of ions that provides the essential information for carbohydrate structural characterization (Mechref and Novotony, Anal. Chem., Volume 75, 4895-4903, 2003). The MS/MS spectrum presents two types of ions due to cross-ring fragmentation that usually involves two bonds on the same sugar residue and the glycosidic bond cleavage between two sugar residues. When the charge of the resulting fragment is located toward the reducing end of the oligosaccharide, then the ions are designated as X ions for cross-ring fragmentation, and Y and Z ions for glycosidic bond fragments. If the charge is located at the nonreducing end, then the ions are designated as A for cross-ring fragmentation, and B and C for the glycosidic bond fragments. The fragmented bond site is indicated with the corresponding letter, a subscript number, and a Greek letter to designate the branched chain involved. Superscript numbers preceding the ions X or A indicates the cleaved bonds in the sugar ring.

Figure 2:
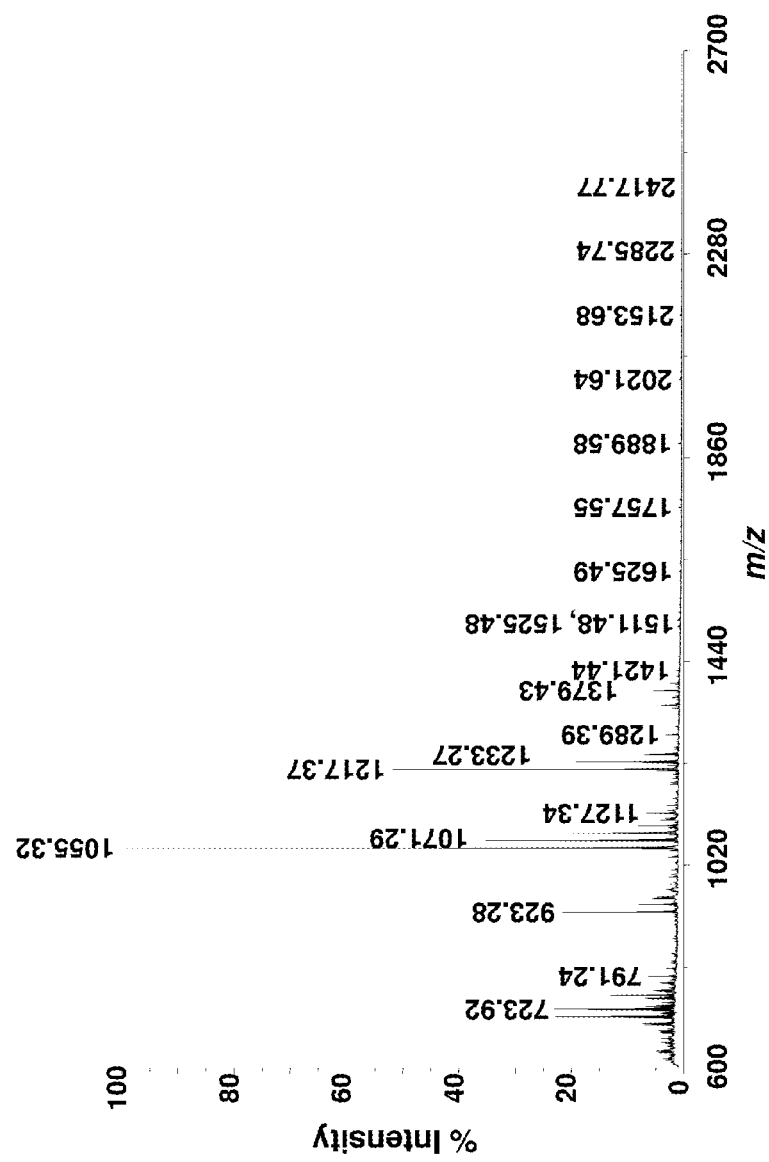
FIG. 2 is a MALDI-TOF mass spectrometry scan of an A6 fraction of cranberry.
Figures 3A, 3B:
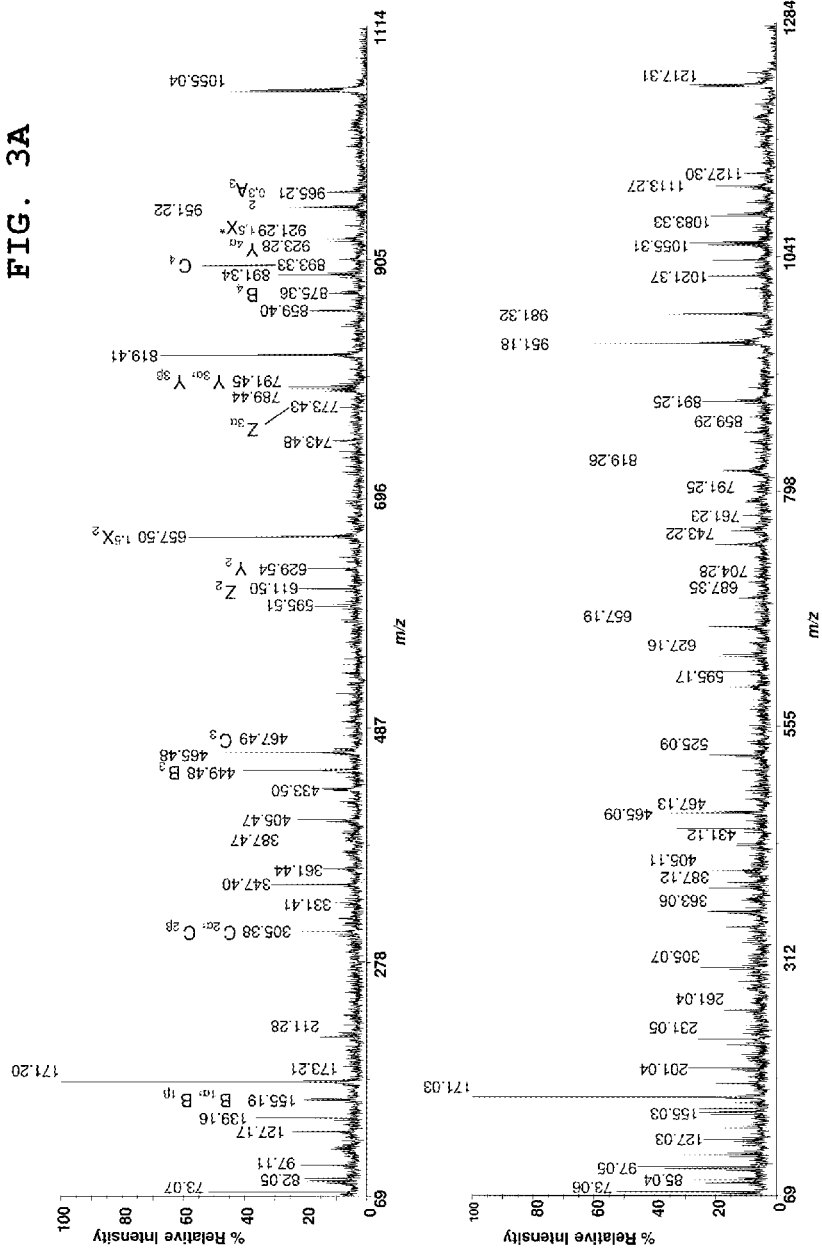
FIGS. 3A and B are Tandem MALDI-TOF spectrum of m/z=1055.32 (A) and m/z=1217.37 (B).
Figure 4:
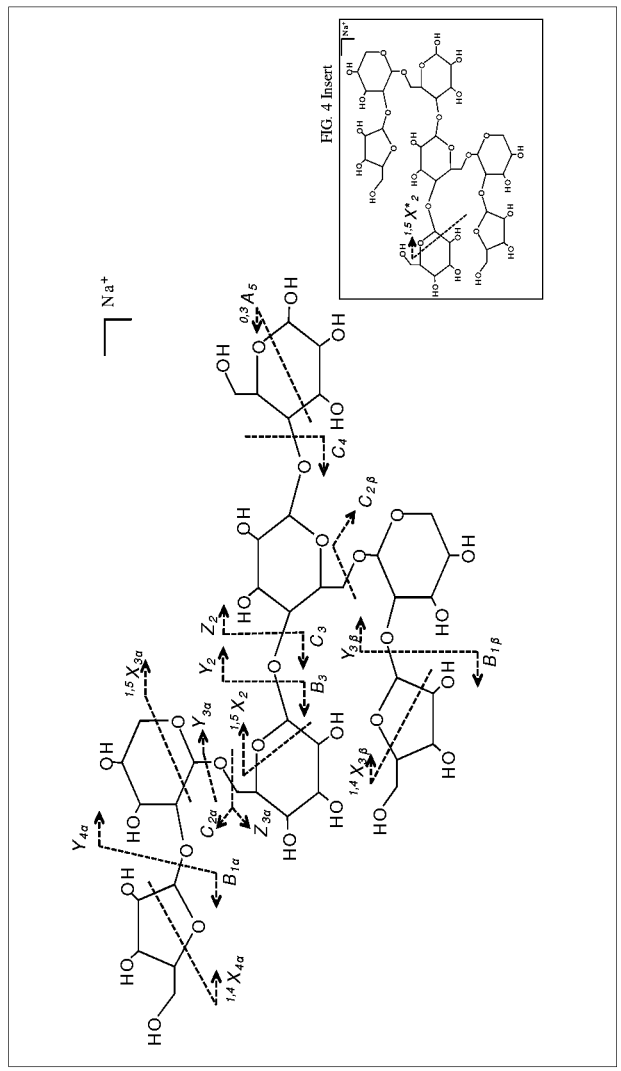
FIG. 4 and FIG. 4 inset are drawings of xyloglucan fragmentation based on MALDI-TOF/TOF MS. The ions retaining the charge at the reducing terminus which is the right end of the depicted structure are designated as X for cross-ring cleavages, and Y and Z for glycosidic bond (bonds between sugar rings) cleavages. Those retaining a charge at the non-reducing terminus (left end of the depicted structure) are designated as A for cross-ring cleavages, and B and C for glycosidic bond cleavages. The fragmentation position is indicated by a dashed line with the arrow pointing toward the reducing end or the non-reducing end. Ions are designated by a subscript number that follows the letter showing the fragment type, corresponding to the sugar ring number along the oligosaccharide chain.

The MS/MS spectrum shown in FIG. 3A corresponds to the sodiated oligosaccharide, [M+Na]$^+$, with a m/z at approximately 1055.32 (FIG. 2). This precursor ion is consistent with an oligosaccharide structure formed by 4 pentoses and 3 hexoses. The ion at m/z approximately 305.3 in the MS/MS spectrum (FIG. 3A) suggests that two pentoses are present as side chains. No ion corresponding to a side antenna with 1, 3 or 4 pentoses is observed in the spectrum. The ion at m/z approximately 893 indicates the loss of a hexose from the precursor ion (1055-162). This suggests that one of the hexoses is not linked to a side chain. However, the spectrum is not dominated by Y or B ions but with ions that are consistent with cross-ring fragmentation as presented in FIG. 4. As the spectrum shows, the cross-ring cleavage (loss approximately 104 amu) at the pentose-end produces the ion at approximately 951, which further loses a pentose to generate the ion at approximately 819, and a hexose to generate the ion at approximately 657. These ions can also be formed by cross-ring fragmentation as labeled in the spectrum according to FIG. 4. Some of the ions are generated from subsequent fragmentation of the approximately 951 fragment, such as the ion at m/z approximately 891 (951-60). The significant ion at m/z approximately 465 could also be explained by subsequent cleavages of the ion at approximately 951 after losing 1 hexose, 2 pentoses, and a cross-ring fragment (951-162-132-132-60=465). Therefore, several ions in FIG. 3A could be produced by multiple fragmentation patterns. Further analysis of the fragmentation pattern indicates that the isobaric structure shown in the FIG. 4 inset is also present. The evidence supporting this structure is found in the ion at m/z approximately 921, which corresponds to the cross-ring cleavage $^{1,5}X^*_2$ of the hexose at the nonreducing terminus (FIG. 4 inset). Therefore, both SSG and GSS structures were present and assigned (Table 4). The spectrum in FIG. 3B is consistent with the structures in FIG. 4 but with an extra hexose. The cross-ring cleavage of the end terminus pentose produces the ion at m/z approximately 1113 (1217-104), but also the loss of a hexose from the precursor ion generates the ion at m/z approximately 1055, and that fragment is consistent with the spectrum and structures in FIG. 3A.

TABLE 4

MALDI-TOF Mass Spectrometry of A6.

| [M + Na]$^+$ | Composition | Structure |
|---|---|---|
| 791.24 | Hex$_3$Pent$_2$ | SGG, XXG |
| 821.26 | Hex$_4$Pent | XGGG |
| 833.25 | Hex$_2$PentdHexHexAMe | |

TABLE 4-continued

MALDI-TOF Mass Spectrometry of A6.

| [M + Na]+ | Composition | Structure |
|---|---|---|
| 923.28 | Hex$_3$Pent$_3$ | SXG, XSG |
| 953.30 | Hex$_4$Pent$_2$ | SGGG |
| 965.29 | Hex$_2$Pent$_2$dHexHexAMe | |
| 1055.32 | Hex$_3$Pent$_4$ | SSG, GSS |
| 1085.33 | Hex$_4$Pent$_3$ | GSXG |
| 1097.34 | Hex$_2$Pent$_3$dHexHexAMe | |
| 1127.34 | Hex$_4$Pent$_3$-Ac | XSGG-Ac |
| 1217.37 | Hex$_4$Pent$_4$ | SSGG |
| 1229.38 | Hex$_2$Pent$_4$dHexHexAMe | |
| 1259.36 | Hex$_4$Pent$_4$-Ac | SSGG-Ac |
| 1289.39 | Hex$_5$Pent$_3$-Ac | XLXG-Ac, XXLG-Ac |
| 1331.37 | Hex$_5$Pent$_3$-Ac$_2$ | UXGGG-Ac, XUGGG-Ac$_2$ |
| 1379.43 | Hex$_5$Pent$_4$ | SSGGG |
| 1421.44 | Hex$_5$Pent$_4$-Ac | GSSGG-Ac |
| 1493.47 | Hex$_2$Pent$_6$dHexHexAMe | |
| 1511.48 | Hex$_5$Pent$_5$ | SSXGG |
| 1525.48 | Hex$_5$Pent$_4$dHex | XUFG |
| 1625.49 | Hex$_2$Pent$_7$dHexHexAMe | |
| 1757.55 | Hex$_2$Pent$_8$dHexHexAMe | |
| 1889.58 | Hex$_2$Pent$_9$dHexHexAMe | |
| 2021.64 | Hex$_2$Pent$_{10}$dHexHexAMe | |
| 2153.68 | Hex$_2$Pent$_{11}$dHexHexAMe | |
| 2285.74 | Hex$_2$Pent$_{12}$dHexHexAMe | |
| 2417.77 | Hex$_2$Pent$_{13}$dHexHexAMe | |

Hex = hexose, Pent = pentose, dHex = deoxyhexose (rhamnose or fucose), Ac = O-acetyl, G = β-D-glucose, X = β-D-glucose with a terminal α-D-xylose substituent at the O-6 position, S = β-D-glucose with α-L-Araf-(1-2)-α-D-Xylp at the O-6 position, L = β-D-glucose with β-D-Galp-(1-2)-α-D-Xylp at the O-6 position, F = β-D-glucose with α-L Fucp-(1-2)-β-D-Galp-(1-2)-α-D-Xylp at the O-6 position, U = β-D-glucose with β-D-Xylp-(1-2)-Xylp with the O-6 position.

Example 3

Nuclear Magnetic Resonance Spectroscopy was used for structural analysis of the oligosaccharides to determine sugar residue identity and connectivity. Fraction A6, obtained from fractionation of the enzyme-treated cranberry hulls described above was dissolved in $^2$H$_2$O (approximately 99.6% $^2$H, Cambridge Isotope Laboratories), lyophilized and redissolved in approximately 0.6 mL of approximately 99.96% enriched $^2$H$_2$O and transferred to a 5 mm NMR tube to obtain a concentration of approximately 5 mM. Most spectra were recorded at about 40 degrees C. on a Bruker Avance-II 700 MHz spectrometer using about a 5 mm xyz-PFG QXI HCNP probe. Data processing was performed using NMRPipe (Delaglio et al., 1994), and analyzed using Sparky (Goddard et al.). All spectra were referenced to the internal $^1$H and $^{13}$C resonances of 4,4-dimethyl-4-silapentan-1-sulfonic acid (DSS). One dimensional $^1$H NMR spectra were acquired using a spectral width of approximately 5,000 Hz, approximately 32,768 points, approximately 70° pulse width, and a recycle time of approximately 2.5 seconds. One dimensional $^{13}$C NMR spectra were acquired at approximately 176 MHz using approximately 65,536 data points, approximately a 70 degree pulse width, and a relaxation time of approximately 2.5 seconds. Gradient enhanced versions of the following experiments were run: Two 2D TOCSY (Total Correlation Spectroscopy), the first at approximately 10 ms and the second at approximately 20 ms mixing time), 2D ROESY (Rotating-frame Overhauser Effect Spetroscopy, approximately 200 ms mixing time), $^1$H-$^{13}$C HSQC (Heteronuclear Single Quantum Correlation), long-range $^1$H-$^{13}$C HSQC, and a $J_{H-C}$—coupled HSQC. The 2D homonuclear experiments were recorded with spectral widths of approximately 5,000 Hz in both dimensions, using approximately 8192 points in the directly-detected dimension, approximately 512 increments in the second dimension, and an approximately 2.5 second delay between scans. These experiments enabled the assignment of resonances and measurement of coupling constants to determine sugar residue identity and connectivity. In addition, an approximately 6 MHz HMBC was performed on a Varian INOVA 500 MHz at about 40 degree C. using a z-PFG PentalProbe, approximately 7,000 Hz sweep width, approximately 8,192 data points in the directly-detected dimension, approximately 550 increments in the second dimension, approximately 64 transients per acquisition, and an approximately 2.5 second delay between scans.

NMR analysis of the anomeric regions in the 1D-$^1$H spectrum (FIG. 5A) reveals that the resonances near approximately 4.5 ppm have H1-H2 coupling constants of $J_{H1-H2}$ of approximately 7-9 Hz, indicating an axial-axial orientation. This is indicative of β-D-Glc and β-D-Gal. The resonances at 4.94 ppm have $J_{H1-H2}$~3.8 Hz, peaks at 4.94, 5.24 5.21, 5.15, 5.31, 5.28 have $J_{H1-H2}$~3.8-4.7 Hz; these suggest an axial-equatorial orientation for monosaccharides with α-configuration. Likewise, the peak at 5.08 has a shoulder that is also 3.5 Hz from the main peak. This is indicative of the pyranoses rhamnose, fucose and xylose, although others may exist. Several peaks in the region of approximately 5.1-5.2 ppm have very small, or indiscernible coupling in the 1D-$^1$H spectrum. These characteristics support an assignment of α-L-Araf. Furanoses such as these undergo rapidly repuckering of their rings, resulting in an averaging of the J values.

There is clear evidence of acetylation of some of the sugars in the fraction (FIG. 5B). Analysis of the HMBC and long-range HSQC-experiments reveals carbonyl carbons with correlations to the C2 positions of many of the α-L-Araf residues.

Analysis of the 2D HSQC indicates that the primary sugar residues are β-Glc, α-Xylp, and α-Araf, as expected from the 1D-$^1$H spectrum and monosaccharide composition analysis. The HSQC reveals that the proton resonances at 4.48-4.57 ppm are separated into two clusters based on their $^{13}$C resonances. One set is centered at a $^{13}$C frequency of ~105 ppm, and corresponds to β-D-Glcp, whereas the other set is at ~107 ppm and corresponds to β-D-Galp. Such β-D-Glcp resonances are commonly found in SG or GS substructure environments (CCRC Xyloglucan NMR Database). Likewise, the β-D-Galp resonances are typically found in L substructures in sequences such as XLF (CCRC NMR Database). The data also allows the assignment of secondary components consisting of α-Rha, and α-Fuc. The presence of α-L-Rha and α-L-Fuc is strongly indicated by H6 methyl resonances, approximately 1.26 ppm (FIG. 5C) that have TOCSY correlations to H5 protons on the directly attached sugar rings (approximately 3.44-4.74 ppm and have $J_{H5-H6}$=approximately 6-7 Hz). In addition, the 1D-$^1$H and the HSQC spectra reveal β-doublets in the approximate range of 4.49-4.65 ppm and 98.4-99.5 ppm ($^1$H and $^{13}$C, respectively). These resonances probably arise from β-D-GlcA, and/or β-D-Gal in an F substructure with an environment such as XFG or LFG (CCRC NMR Database).

The anomeric proton orientations (α or β) were confirmed by means of their C—H coupling constants $J_{C1-H1}$ of approximately 160 Hz, and those with an equatorial H-1 have values of approximately 170 Hz (Bock et al., Tetrahedron Lett, Volume 13, 1037-1040, 1973). A summary of the anomeric chemical shifts, their assignments (with orientations), and likely substructures can be found in Table 5. These assignments are based on the available $^1$H-$^1$H coupling information, and are fully consistent with literature values of both the $^1$H and $^{13}$C chemical shifts (Bock et al., Adv. Carbohydr. Chem. Biochem. Volume 41, 27-66, 1983 and Adv. Carbohydr. Chem. Biochem. Volume 42, 193-225, 1984; Hannify et al., Carbohydr. Res. Volume 319, 124-132, 1999; Verhuis et al., 2001, supra; Hoffman et al., 2005, supra; Mazzola et al., Carbohydr. Res. Volume 346, 759-768, 2011). While the use of coupling constants is considered to be the most reliable method of assigning sugar resonances (Coxon, Adv. Carbohydr. Chem. Biochem. Volume 62, 17-82, 2009; Mazzola et al., 2001, supra), the use of tabulations of chemical shifts is an accepted method of assignment owing to the difficulties of analyzing highly congested spectra. The possible substructures listed in Table 5 are likewise determined from chemical shift information, and confirm what was observed using mass spectrometry.

The HMBC and HSQC experiments indicate the presence of aromatic components having $^1$H resonances between approximately 7.5-9.7 ppm and $^{13}$C resonances in the range of approximately 90-180 ppm. These resonances are consistent with polyphenolic anthocyanins or proanthocyanidin compounds, although the actual structures have not been established. The spectra do suggest that they are linked to several sugars, however, this has not yet been proven. Similar chemical species have been identified by others (Yan et al., J. Agric. Food Chem., Volume 50, 5844-5849, 2002).

TABLE 5

NMR anomeric resonance assignments

| Sugar† | H-1 | C-1 | Substructures†† | Example Substructure Environment |
|---|---|---|---|---|
| β-Glcp | 4.48-4.56 | 104.8-105.7 | G | SG or GS |
| β-Galp | 4.52-4.57 | 106.9-107.4 | L | XLF |
| β-GlcAp, | 4.49-4.67 | 98.4-99.5 | | |
| β-Galp | | | F | (L/F)FG |
| α-Xylp | 4.916-4.95 | 100.9-101.7 | S or X | |
| α-L-Araf | 5.07-5.23 | 109-112.1 | S | XSG, GSG, SSG, GSS |
| α-L-Rha | 5.05-5.15 | 100.6-101.7 | | |
| α-L-Fuc | 5.21 | 94.5 | F | XFG |

†Based on $^1$H-$^1$H and $^1$H-$^{13}$C anomeric coupling and literature values of $^1$H and $^{13}$C chemical shifts
††Determined by comparison to published chemical shifts of oligosaccharides Example 4

To test for biological activity of the anti-microbial adhesion inhibitory fraction A6 of the invention, human bladder epithelial cells T24 (ATCC #HTB-4) and *Escherichia coli* 1161 (ATCC #BAA-1161) were seeded in a 24-well plate and set to grow to confluence at about 37 degrees in an about 5% $CO_2$ incubator. The cells were then treated with ultraviolet light. Approximately 1 mL of LB medium (Muler Hinton II Broth) was added to each well. Fraction A6 samples were dissolved in DMSO, centrifuged at approximately 3,000 rpm for about 15 minutes at approximately 4 degrees C., approximately 50 μL of supernatant was added to the wells. Phosphate Buffer Solution (PBS) or DMSO was used as a negative control. Approximately 20 μL of *E. coli* solution was added to each well. After about three hours of incubation, the solution in a plate was aspirated off. Wells were washed twice with PBS. Bacteria bound to the cell membrane were lysed with microbial viability buffer. The ATP level, an indicator of viable cells, was read optically by a plate reader. The percent inhibition of bacterial adhesion was calculated as: (ATP negative control-ATP sample)/ATP negative control)×100%.

The effect of anti-microbial adhesion inhibitory fraction A6 on bacterial adhesion was also determined with *E. coli* O157:H7 (ATCC #BAA-1883) and human colonic epithelial cells HT29 (ATCC #HTB-38) using a standard assay reported earlier (Rhoades et al., 2008, supra).

The biological activity of anti-microbial adhesion inhibitory fraction A6 was determined with bacterial adhesion assays using the uropathogenic *E. coli* 1161 and the verotoxigenic *E. coli* O157.H7 strains. The lowest concentration of A6, approximately 1.25-10 mg/ml, blocked adhesion on *E. coli* 1161 to T24 human bladder epithelial cells with approximately 20 mg/ml or above concentrations no different from the PBS control (Table 6), The A6 fraction had much higher anti-adhesion activity compared to A1 (FIG. 6). The cranberry concentrate powder (A1) was much more enriched in pectic oligosaccharides compared to the xyloglucan oligosaccharide enriched A6 fraction. The higher levels of xyloglucan oligosaccharides correlated with the higher anti-adhesion activity.

A similar non-dose-dependent response was observed for the anti-adhesion activity of A6 in the bacterial adhesion assay reported earlier by Rhoades et al. (2008, supra). In this assay, A6 was able to block the adhesion of *E. coli* O157:H7 to human colonic epithelial HT29 cells at approximately 0.15-2.5 mg/ml concentrations (Table 7). Uropathogenic (P-fimbriated) and verotoxigenic strains of *E. coli* utilize the same α-Gal-(1-4)-Gal terminal oligosaccharide receptor for adhesion to epithelial cells (Hotchkiss and Buddington, Functional Food Review, Volume 3(3), 119-134, 2011). Therefore, this second bacterial adhesion assay confirms that the A6 xyloglucan oligosaccharide fraction blocks the specific interaction required for adhesion of these pathogens to two different human epithelial cells.

TABLE 6

*E. coli* 1161 adhesion assay using fraction A6 (dry weight mg/ml)

| Reading | PBS | 0.5% DMSO | A6, 1.25 mg/ml | A6, 2.5 mg/ml | A6, 5.0 mg/ml | A6, 10 mg/ml | A6, 20 mg/ml | A6, 40 mg/ml |
|---|---|---|---|---|---|---|---|---|
| 1 | 1394 | 809 | 685 | 900 | 887 | 866 | 1401 | 1315 |
| 2 | 1465 | 869 | 732 | 973 | 942 | 946 | 1359 | 1512 |
| 3 | 1363 | | 680 | 860 | 740 | 854 | 1294 | 1434 |
| Average | 1407 | 839 | 699 | 911 | 856 | 889 | 1351 | 1420 |
| Stdev | 52.29 | 42.43 | 28.69 | 57.30 | 104.43 | 50.01 | 53.91 | 99.21 |
| CV % | 3.72 | 5.06 | 4.10 | 6.29 | 12.20 | 5.63 | 3.99 | 6.99 |

TABLE 7

Adhesion of *E. coli* O157:H7 to HT29 cells in the presence of fraction A6 (dry weight mg/ml).

| S. No. | A6 (Mg/ml) | Adhesion relative to control (%) |
|---|---|---|
| 1 | 0.15 | 13.8% |
| 2 | 0.3 | 5% |
| 3 | 0.5 | 12.2% |
| 4 | 2.5 | 15.5% |

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

We claim:

1. An anti-microbial composition, wherein said anti-microbial composition comprises a tablet or capsule having an effective amount of an anti-microbial adhesion inhibitory composition to inhibit the adhesions of bacteria to cells having α-Gal-(1-4)-β-Gal terminal oligosaccharide receptors for adhesion prepared by the method comprising the steps of:
   (a) providing cranberry hulls
   (b) treating said cranberry hulls with a pectinase in amounts sufficient to depectinize said hulls to form an enzyme treated composition,
   (c) removing debris from said enzyme treated composition using a method selected from the group consisting of decantation, centrifugation, and combinations thereof to form a first liquid,
   (d) spray drying said first liquid to form composition A1,
   (e) fractionating said composition A1 using C18 Flash Chromatography to produce composition A2
   (f) freeze drying said composition A2
   (g) purifying composition A2 using LH20 gel column chromatography to produce said anti-microbial adhesion inhibitory composition A6,
   (h) freeze drying said anti-microbial adhesion inhibitory composition A6 to produce a crystalline powder,
   (i) mixing said crystalline powder with a carrier to provide an anti-microbial adhesion inhibitory composition.

2. The composition of claim 1, wherein said tablet or capsule comprises a medicament, a nutritional composition, or a pharmaceutical composition.

3. An anti-microbial composition, wherein said anti-microbial composition comprises a tablet or capsule having an effective amount of an anti-microbial adhesion inhibitory composition to inhibit the adhesions of bacteria to cells having α-Gal-(1-4)-β-Gal terminal oligosaccharide receptors for adhesion prepared comprising the steps of:
   (a) providing cranberry hulls
   (b) treating said cranberry hulls with a pectinase in amounts sufficient to depectinize said hulls to form an enzyme treated composition,
   (c) removing debris from said enzyme treated composition using a method selected from the group consisting of decantation, centrifugation, and combinations thereof to form a first liquid,
   (d) spray drying said first liquid to form composition A1,
   (e) fractionating said composition A1 using C18 Flash Chromatography to produce composition A2
   (f) freeze drying said composition A2
   (g) purifying fraction A2 LH20 using gel column chromatography to produce said anti-microbial adhesion inhibitory composition A6,
   (h) freeze drying said anti-microbial adhesion inhibitory composition A6 to produce a crystalline powder,
   (i) mixing said crystalline powder with a carrier to provide an anti-microbial adhesion inhibitory composition;
   wherein said anti-microbial adhesion inhibitory composition comprises arabino-xyloglucan with an SSG structure:

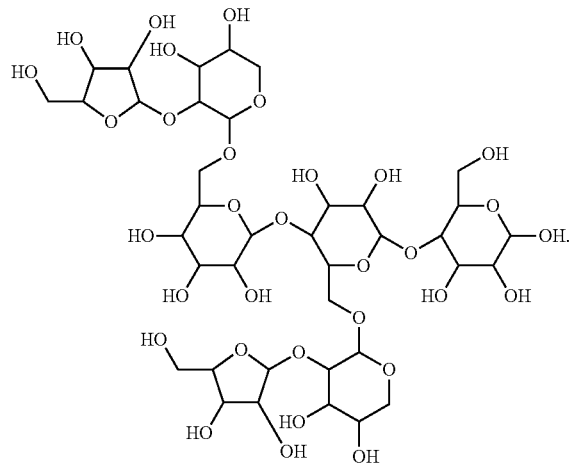 [SMILES: OCC1OC(OC2C(OCC3OC(OC4C(COC5OCC(O)C(O)C5OC5OC(CO)C(O)C5O)OC(OC5C(CO)OC(O)C(O)C5O)C(O)C4O)C(O)C(O)C3O)OCC(O)C2O)C(O)C1O]

4. The composition of claim 3, wherein said tablet or capsule comprises a medicament, a nutritional composition, or a pharmaceutical composition.

5. A method for reducing the adhesion of bacteria to cells having α-Gal-(1-4)-Gal terminal oligosaccharide receptors for adhesion comprising administering to said cells an effective amount of the composition of claim 1 or the composition of claim 3.

* * * * *